United States Patent
Cullen et al.

(10) Patent No.: US 9,687,581 B2
(45) Date of Patent: *Jun. 27, 2017

(54) WOUND DRESSINGS FOR THE CONTROLLED RELEASE OF THERAPEUTIC AGENTS

(71) Applicant: KCI USA, Inc., San Antonio, TX (US)

(72) Inventors: Breda Mary Cullen, Skipton (GB); Sara Jayne Gregory, West Yorkshire (GB)

(73) Assignee: KCI USA, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/507,099

(22) Filed: Oct. 6, 2014

(65) Prior Publication Data

US 2015/0098985 A1    Apr. 9, 2015

Related U.S. Application Data

(62) Division of application No. 10/579,897, filed as application No. PCT/GB2004/004874 on Nov. 18, 2004, now Pat. No. 8,858,987.

(30) Foreign Application Priority Data

Nov. 24, 2003 (GB) .................................. 0327326.5

(51) Int. Cl.
| | |
|---|---|
| *A61L 15/32* | (2006.01) |
| *A61L 15/44* | (2006.01) |
| *A61L 15/18* | (2006.01) |
| *A61K 38/08* | (2006.01) |
| *A61K 38/48* | (2006.01) |

(52) U.S. Cl.
CPC .............. *A61L 15/32* (2013.01); *A61L 15/18* (2013.01); *A61L 15/44* (2013.01); *A61L 2300/412* (2013.01); *A61L 2300/434* (2013.01); *A61L 2300/45* (2013.01); *A61L 2300/604* (2013.01)

(58) Field of Classification Search
CPC .......... A61L 15/32; A61L 15/44; A61L 15/18; A61L 2300/412; A61L 2300/434; A61L 2300/45; A61L 2300/604; A61K 38/08; A61K 38/48

See application file for complete search history.

(56) References Cited

U.S. PATENT DOCUMENTS

| | | | |
|---|---|---|---|
| 5,612,321 A | 3/1997 | Nguyen | |
| 5,667,501 A | 9/1997 | Fowler et al. | |
| 5,770,229 A | 6/1998 | Tanihara et al. | |
| 6,472,143 B1 | 10/2002 | Mikolajczyk et al. | |
| 2002/0012693 A1* | 1/2002 | Cohen et al. ................. | 424/446 |

FOREIGN PATENT DOCUMENTS

| | | | |
|---|---|---|---|
| EP | 0541391 A1 | | 5/1993 |
| GB | 1280631 A | | 7/1972 |
| GB | 2 382775 A | * | 6/2003 |
| GB | 2382775 A | | 6/2003 |
| WO | 2004/030711 A1 | | 4/2004 |
| WO | 2004/096302 A1 | | 11/2004 |

OTHER PUBLICATIONS

Xing et al. ("Control of Breast Tumor Cell Growth Using a Targeted Cysteine Protease Inhibitor" in Cancer Research 58, 904-909, Mar. 1, 1998).*
Winston et al. current protocols in molecular biology, 2001 online.*
Ulbrich et al. (1980) Biomaterials 1, 199-204.
Veronese, F.M. and Morpurgo, M (1999) Bioconjugation in Pharmaceutical chemistry II Farmaco, 54, 497-516.
Ulbrich, K., et al (2000) Polymeric drugs based on conjugates of synthetic and natural marcomolecules I. Synthesis and physicochemical characterisation. Journal of controlled release 64, 63-79.

* cited by examiner

*Primary Examiner* — Blessing M Fubara

(57) ABSTRACT

A wound dressing material for controlled activation of a wound healing therapeutic compound in the presence of a protease enzyme in a wound fluid, the material comprising: a medically acceptable polymer; a wound healing therapeutic agent; an inhibitor of the protease enzyme; and a linker group which is cleavable by the protease enzyme, wherein the activities of both the wound healing therapeutic agent and the inhibitor are increased by contacting the wound dressing material with a would fluid containing the protease enzyme. For example, the enzyme may be a matrix metalloproteinase, the therapeutic agent may be a reactive oxygen scavenger, and the inhibitor may be a tissue inhibitor of metalloproteinase (TIMP).

17 Claims, No Drawings

SEQUENCE LISTING

```
<160> NUMBER OF SEQ ID NOS: 25

<210> SEQ ID NO 1
<211> LENGTH: 9
<212> TYPE: PRT
<213> ORGANISM: Homo sapiens

<400> SEQUENCE: 1

Lys Gly Ala Ala Ala Lys Ala Ala Ala
1               5

<210> SEQ ID NO 2
<211> LENGTH: 4
<212> TYPE: PRT
<213> ORGANISM: Homo sapiens

<400> SEQUENCE: 2

Ala Ala Pro Val
1

<210> SEQ ID NO 3
<211> LENGTH: 4
<212> TYPE: PRT
<213> ORGANISM: Homo sapiens

<400> SEQUENCE: 3

Ala Ala Pro Leu
1

<210> SEQ ID NO 4
<211> LENGTH: 4
<212> TYPE: PRT
<213> ORGANISM: Homo sapiens

<400> SEQUENCE: 4
```

Ala Ala Pro Phe
1

<210> SEQ ID NO 5
<211> LENGTH: 4
<212> TYPE: PRT
<213> ORGANISM: Homo sapiens

<400> SEQUENCE: 5

Ala Ala Pro Ala
1

<210> SEQ ID NO 6
<211> LENGTH: 4
<212> TYPE: PRT
<213> ORGANISM: Homo sapiens

<400> SEQUENCE: 6

Ala Tyr Leu Val
1

<210> SEQ ID NO 7
<211> LENGTH: 6
<212> TYPE: PRT
<213> ORGANISM: Homo sapiens
<220> FEATURE:
<221> NAME/KEY: X
<222> LOCATION: (3)..(3)
<223> OTHER INFORMATION: X may be any amino acid
<220> FEATURE:
<221> NAME/KEY: X
<222> LOCATION: (6)..(6)
<223> OTHER INFORMATION: X may be any amino acid

<400> SEQUENCE: 7

Gly Pro Xaa Gly Pro Xaa
1               5

<210> SEQ ID NO 8
<211> LENGTH: 6
<212> TYPE: PRT
<213> ORGANISM: Homo sapiens
<220> FEATURE:
<221> NAME/KEY: X
<222> LOCATION: (6)..(6)
<223> OTHER INFORMATION: X may be any amino acid

<400> SEQUENCE: 8

Gly Pro Leu Gly Pro Xaa
1               5

<210> SEQ ID NO 9
<211> LENGTH: 6
<212> TYPE: PRT
<213> ORGANISM: Homo sapiens
<220> FEATURE:
<221> NAME/KEY: X
<222> LOCATION: (6)..(6)
<223> OTHER INFORMATION: X may be any amino acid

<400> SEQUENCE: 9

Gly Pro Ile Gly Pro Xaa
1               5

<210> SEQ ID NO 10
<211> LENGTH: 5
<212> TYPE: PRT

```
<213> ORGANISM: Homo sapiens
<220> FEATURE:
<221> NAME/KEY: X
<222> LOCATION: (5)..(5)
<223> OTHER INFORMATION: X may be any amino acid

<400> SEQUENCE: 10

Ala Pro Gly Leu Xaa
1               5

<210> SEQ ID NO 11
<211> LENGTH: 6
<212> TYPE: PRT
<213> ORGANISM: Homo sapiens
<220> FEATURE:
<221> NAME/KEY: X
<222> LOCATION: (5)..(5)
<223> OTHER INFORMATION: X is D-arginine
<220> FEATURE:
<221> NAME/KEY: X
<222> LOCATION: (6)..(6)
<223> OTHER INFORMATION: X may be any amino acid

<400> SEQUENCE: 11

Pro Leu Gly Pro Xaa Xaa
1               5

<210> SEQ ID NO 12
<211> LENGTH: 7
<212> TYPE: PRT
<213> ORGANISM: Homo sapiens
<220> FEATURE:
<221> NAME/KEY: X
<222> LOCATION: (7)..(7)
<223> OTHER INFORMATION: X may be any amino acid

<400> SEQUENCE: 12

Pro Leu Gly Leu Leu Gly Xaa
1               5

<210> SEQ ID NO 13
<211> LENGTH: 7
<212> TYPE: PRT
<213> ORGANISM: Homo sapiens

<400> SEQUENCE: 13

Pro Gln Gly Ile Ala Gly Trp
1               5

<210> SEQ ID NO 14
<211> LENGTH: 5
<212> TYPE: PRT
<213> ORGANISM: Homo sapiens
<220> FEATURE:
<221> NAME/KEY: X
<222> LOCATION: (5)..(5)
<223> OTHER INFORMATION: X is methylated histidine

<400> SEQUENCE: 14

Pro Leu Gly Cys Xaa
1               5

<210> SEQ ID NO 15
<211> LENGTH: 5
<212> TYPE: PRT
<213> ORGANISM: Homo sapiens

<400> SEQUENCE: 15
```

Leu Gly Leu Trp Ala
1               5

<210> SEQ ID NO 16
<211> LENGTH: 7
<212> TYPE: PRT
<213> ORGANISM: Homo sapiens

<400> SEQUENCE: 16

Pro Leu Ala Leu Trp Ala Arg
1               5

<210> SEQ ID NO 17
<211> LENGTH: 7
<212> TYPE: PRT
<213> ORGANISM: Homo sapiens

<400> SEQUENCE: 17

Pro Leu Ala Tyr Trp Ala Arg
1               5

<210> SEQ ID NO 18
<211> LENGTH: 7
<212> TYPE: PRT
<213> ORGANISM: Homo sapiens

<400> SEQUENCE: 18

Pro Leu Gly Met Trp Ser Arg
1               5

<210> SEQ ID NO 19
<211> LENGTH: 4
<212> TYPE: PRT
<213> ORGANISM: Homo sapiens

<400> SEQUENCE: 19

Gly Arg Gly Asp
1

<210> SEQ ID NO 20
<211> LENGTH: 6
<212> TYPE: PRT
<213> ORGANISM: Homo sapiens

<400> SEQUENCE: 20

Gly Arg Gly Asp Asn Pro
1               5

<210> SEQ ID NO 21
<211> LENGTH: 5
<212> TYPE: PRT
<213> ORGANISM: Homo sapiens

<400> SEQUENCE: 21

Gly Arg Gly Asp Ser
1               5

<210> SEQ ID NO 22
<211> LENGTH: 7
<212> TYPE: PRT
<213> ORGANISM: Homo sapiens

<400> SEQUENCE: 22

Gly Arg Gly Asp Ser Pro Lys
1               5

```
<210> SEQ ID NO 23
<211> LENGTH: 7
<212> TYPE: PRT
<213> ORGANISM: Homo sapiens

<400> SEQUENCE: 23

Pro Tyr Ala Tyr Trp Met Arg
1               5

<210> SEQ ID NO 24
<211> LENGTH: 6
<212> TYPE: PRT
<213> ORGANISM: Homo sapiens

<400> SEQUENCE: 24

Phe Arg Ser Ser Arg Gln
1               5

<210> SEQ ID NO 25
<211> LENGTH: 9
<212> TYPE: PRT
<213> ORGANISM: Homo sapiens

<400> SEQUENCE: 25

Met Ile Ser Leu Met Lys Arg Pro Gln
1               5
```

WOUND DRESSINGS FOR THE CONTROLLED RELEASE OF THERAPEUTIC AGENTS

DETAILED DESCRIPTION

This application is a Divisional of U.S. patent application Ser. No. 10/579,897 filed May 19, 2006 which claims priority to PCT/GB04/04874 filed Nov. 18, 2004.

The present invention relates to wound dressing materials that provide controlled release of therapeutic agents when placed in contact with a wound fluid.

The amount and composition of wound fluid (exudate) produced by a wound depends on the type of wound and the history of wound healing. For example, surgical wounds have an acute inflammatory phase of a few days during which discharge is significant, after which the rate of exudate production can be expected to fall sharply. Chronic wounds, such as ulcers, produce wound fluid containing elevated levels of matrix metalloproteinase (MMP) enzymes. Burns produce large amounts of wound exudate having characteristic properties. Pain is also associated with characteristic protease enzymes in wound fluid. Biochemically, pain is experienced when there is an increase of kinins (bradykinin) in the area of the wound. Kinins are produced by the proteolytic breakdown of kininogen, and the protease responsible for this is kallikrein.

Infected wounds generally produce substantially more exudate than non-infected wounds, and the composition of the wound fluid is different. In particular, it has been found that levels of elastase are elevated in infected wounds, both during and immediately before the onset of clinical signs of wound infection.

U.S. Pat. No. 5,770,229 describes medical polymer gels for use in medical applications, including wound dressings. The polymer molecules are covalently bonded to drug molecules through linker groups that can be cleaved by an enzyme such as elastase. The drug may for example be an antimicrobial, or a growth factor, or a tissue inhibitor of metalloproteinase (TIMP).

Wound fluids can also contain elevated concentrations of reactive oxygen species such as hydroxyl radicals (.OH), singlet oxygen ($^1O_2$), hydroperoxyl radicals (.OOH), superoxideradical anions (.$O2^-$), and hydrogen peroxide ($H_2O_2$). Under mild oxidative stress, it is thought that hydrogen peroxide ($H_2O_2$) is the dominant species present, being formed rapidly from superoxide by the enzyme superoxide dismutase. Under mild oxidative stress conditions when hydrogen peroxide levels are slightly raised (around $10^{-8}$ to $10^{-4}$ molar), it has been found that the rate of cell proliferation in fibroblast cultures is stimulated. Furthermore, the presence of a low level of reactive oxygen species can be advantageous in the early stages of wound healing by both attracting and activating macrophages which engulf and kill bacteria and release cytokines and growth factors. However, prolonged and more severe oxidative stress may delay healing because it will produce chronic inflammation, divert available energy supply towards antioxidant defense at the expense of tissue reconstruction, and increase levels of matrix metalloproteinases which cause tissue breakdown. In more severe cases, elevated levels of reactive oxygen species can give rise to hydrogen peroxide-induced senescence or apoptosis (that is, programmed cell death) or tissue necrosis (that is, uncontrolled cell death and therefore permanent tissue damage).

Accordingly, the healing of chronic wounds may be assisted by the use of antioxidant wound dressings that react specifically with excess reactive oxygen species such as those listed above and hence reduce the level of oxidative stress. However, it may not be desirable to eliminate reactive oxygen species completely, reactive oxygen species at low concentrations do have a positive role in wound healing.

U.S. Pat. No. 5,667,501 describes compositions comprising chemically modified polymers grafted with chemical groups that confer antioxidant activity as measured by a diphenylpicrylhydrazyl (DPPH) test and that also generate low levels of hydrogen peroxide by reaction with molecular oxygen in the wound bed to stimulate macrophage activity and fibroblast proliferation. The compositions may be used to promote the healing of chronic wounds. Preferably, the polymer is a polymer bearing hydroxyl, carbonyl or amide functional groups, or a polysaccharide bearing hydroxyl functional groups, said functional groups having been converted to derivatives that are persistent free radicals or precursors of persistent free radicals, that is to say they are free radical scavenging antioxidant groups.

U.S. Pat. No. 5,612,321 describes compositions comprising polysaccharides grafted with antioxidants on at least one hydroxyl group of the polysaccharide. The compositions may be used inter alia to promote the healing of chronic wounds. Preferably, the polysaccharide is hyaluronic acid and the antioxidant group comprises a phenol group.

The above-described antioxidant dressings will tend to remove all reactive oxygen from the vicinity of the wound under treatment, and thereby the beneficial effects on wound healing of low concentrations of reactive oxygen are lost.

In a first aspect, the present invention provides a wound dressing material for controlled activation of a wound healing therapeutic agent in the presence of a protease enzyme in a wound fluid, the wound dressing material comprising: [0011] a medically acceptable polymer; [0012] a wound healing therapeutic agent; [0013] an inhibitor of the protease enzyme; and [0014] a linker group which is cleavable by the protease enzyme, wherein the activities of both the wound healing therapeutic agent and the inhibitor are increased by contacting the wound dressing material with a wound fluid containing the protease enzyme.

The wound healing therapeutic agent and the inhibitor are initially bound to, and/or entrapped within a matrix of, the polymer. In this state the therapeutic agent and the inhibitor have reduced activity, and often have little or no activity. The reaction between the linker groups and the enzyme usually effects release of substantially free (unbound) therapeutic agent and inhibitor into the wound fluid. In some embodiments, the therapeutic agent and/or the inhibitor may remain bound to the polymer or a polymer fragment after activation by the enzyme.

The wound dressing materials according to the present invention are more responsive to the condition of a wound over time, because the inhibitor prevents excessive or uncontrolled release of the therapeutic agent in the presence of elevated levels of the protease enzyme. The release of the inhibitor by the action of the enzyme means that a further supply of the enzyme is needed to prompt further release of the therapeutic agent after an initial release has been accomplished.

By an "increase" in the activity of the therapeutic agent and the inhibitor we include the situation where the activity of the therapeutic agent increases by at least 1.5, 2-, 3-, 4-, 5-, 6-, 7-, 8-, 9-, 10- or 15-fold in a the presence of the enzyme.

Typically, the rate of release of the therapeutic agent and the inhibitor increases by at least 1.5, 2-, 3-, 4-, 5-, 6-, 7-, 8-, 9-, 10- or 15-fold in the presence of wound fluid containing the enzyme at activity twice that of normal healthy serum. Preferably, there is no release of the therapeutic agent and the inhibitor in the absence of the enzyme.

There are three principal types of dressing material according to the invention. In the first type of material, the wound healing therapeutic agent and the inhibitor are dispersed or encapsulated or physically entrapped in a matrix of the medically acceptable polymer, and the polymer comprises the linker group. The polymer itself is degraded by the enzyme in the wound fluid through the cleavage of the linker groups, and this breakdown of the polymer releases the wound healing therapeutic agent and the inhibitor into the wound fluid.

In the wound dressing materials of this type, the polymer itself may comprise the linker group as part of the main polymer chain. For example, if the enzyme is an elastase, then the polymer could be an elastin. Alternatively, the polymer may be a medically acceptable polymer crosslinked by the linker group.

The degree of crosslinking of the polymers should be sufficient such that the rate of release of the therapeutic agent and the inhibitor increases in the presence of the enzyme. Preferably, the degree of crosslinking of the polymers should be sufficient to render the matrix sufficiently impermeable to the molecule to be delivered so that the therapeutic agent and the inhibitor are only released in the presence of the target enzyme. This will be dependent on the molecular weight of the therapeutic agent and the inhibitor.

In the second main type of wound dressing material according to the invention, the wound healing therapeutic agent and/or the inhibitor are conjugated to the medically acceptable polymer by the linker group. Preferably, the wound healing therapeutic agent and the inhibitor are each separately conjugated to the medically acceptable polymer by the linker group. The wound healing therapeutic agent and the inhibitor are then both released by cleavage of the linker groups by the enzyme, without any need for degradation of the polymer itself.

In the third main type of wound dressing material according to the invention, the wound healing therapeutic agent is itself conjugated to the inhibitor by the linker group. Cleavage of the linker group thereby activates both the therapeutic agent and the inhibitor. The therapeutic agent and/or the inhibitor may each independently be conjugated to the polymer as well.

The term "polymer" as used herein includes homopolymers and copolymers (e.g. random copolymers, alternating copolymers and block copolymers).

In theory, any polymer containing groups to which the cleavable groups and/or the therapeutic agent and inhibitor can be attached may be used, although of course the skilled person will appreciate that considerations such as toxicity should be taken into account. Similarly, the polymers used should not be immunogenic.

In certain embodiments, the polymers are synthetic polymers. Examples of synthetic polymers include polyvinyl alcohol, polyethylene glycerol, PVP, polyolefins, fluoropolymers, hydropolymers from vinyl esters, vinyl ethers, carboxy vinyl monomers, meth(acrylic) acid, acrylamide, N-vinyl pyrrolidone, acylamidopropanem acylamidopropane, PLURONIC (Maleic acid, NN-dimethylacrylamide diacetone acrylamide acryloyl, morpholine and mixtures thereof. Suitable synthetic polymers include non-ionic surfactants, polyalkoxylated alcohols, alkyl or dialkyl polyglycerol compounds, polyethyloxylated alcohols, and polymers (including homopolymers and copolymers) of acrylamide (e.g. N-(2-hydroxypropyl)methacrylamide (HPMA).

Alternatively, natural polymers such as carbohydrates (e.g. dextran, chitin or chitosan); natural peptides or proteins (collagens, elastins, fibronectins, or even soluble proteins such as albumin); modified biopolymers such as carboxymethyl cellulose, hydroxyethyl cellulose and oxidized regenerated cellulose; or semi synthetic peptides (made by using a peptide synthesizer or by recombinant techniques) may be used.

In a preferred embodiment of the first mode of the invention, polymers of N-(2-hydroxypropyl) methyacrylamide (HPMA) are cross-linked with the cleavable peptide. In this regard, reference is made to Ulbrich et al. (1980) Biomaterials 1, 199-204, which details the crosslinking of HPMA polymers by peptides.

The cleavable cross-linkages generally comprise cleavable oligopeptidic sequences or cleavable oligosaccharides, each typically of twenty residues or fewer, for example from 3 to 15 residues.

The rate of release of the therapeutic agent and the inhibitor will depend on a number of factors, including the length of the cleavable linker sequences. Ulbrich et al. noted that extension of the peptidic linkers by one amino acid residue to give a peptidic linker of four amino acids caused a pronounced rise in the rate of cleavage of the polymeric substrates. Ulbrich et al. reported that extension of the oligopeptidic sequence led to a decrease in the steric hindrance by polymer chain and thus to an increase in degradability.

Steric hindrance may also be reduced by coupling the cleavable oligopeptidic sequence to the polymer by means of an appropriate spacer. Thus, the oligopeptidic sequences may couple the polymers directly (in which case the cross-linkage consists of the oligopeptidic sequence) or by means of an appropriate spacer. Suitable conjugation methods incorporating spacers are described in U.S. Pat. No. 5,770,229.

The following paper gives a useful review of bioconjugation techniques for use in pharmaceutical chemistry: Veronese, F. M. and Morpurgo, M (1999) Bioconjugation in Pharmaceutical chemistry II Farmaco, 54, 497-516. This paper describes in detail the chemistry of each amino acid and which ones are most suitable for use in bioconjugation techniques. For example, it demonstrates that conjugation would occur by nucleophile to electrophile attacks. The amino acid side chains R—S—, R—NH$_2$, R—COO— and =R—O— are well suited to bioconjugation (to natural or synthetic molecules).

In addition this paper indicates and gives examples of a wide range of structures and chemical groups that the peptides (containing amino (e.g. lysine), carboxyl (COO—) or cystyl groups (R—SH) can bind to.

With regard to conjugation techniques, see also Ulbrich, K., et al (2000) Polymeric drugs based on conjugates of synthetic and natural macromolecules I. Synthesis and physico-chemical characterisation. Journal of controlled release 64, 63-79. This reference describes how antibodies, peptides or proteins can be conjugated to synthetic polymers (e.g. poly HPMA).

The rate of degradation will not only depend on the number of amino acids but also on the nature of the amino acids comprising the cross-links. This dependency arises from the substrate specific nature of proteases. The region of the enzyme where interaction with the substrate takes place is known as the "active site" of the enzyme. The active site performs the dual role of binding the substrate while catalysing the reaction, for example cleavage. Studies of the structures of the complexes of proteolytic enzymes with peptides indicate that the active site of these enzymes is relatively large and binds to several amino acid residues in the peptide. Thus, the degradability of a particular bond in a peptide chain depends not only on the nature of the structure near the cleaved bond, but also on the nature of the amino acid residues which are relatively remote from the cleaved bond, but play an important part in holding the enzyme in position during hydrolysis.

The present invention is suitable for use with a wide variety of enzyme and substrate systems. Typically, the enzyme is selected such that elevated levels of the enzyme in wound fluid are associated with pain, wound infection or wound chronicity. Usually, the enzyme is a protease, and the linker group comprises an oligopeptidic sequence which is a substrate for the protease.

In certain embodiments protease is elastase. Elastase levels are elevated in a range of wound healing disorders, including infected wounds and chronic wounds. In such embodiments, suitable substrate linkers may include one or more of the oligopeptidic sequences lys-gly-ala-ala-ala-lys -Ala-Ala-Ala- (SEQ ID NO:1), Ala-Ala-Pro-Val (SEQ ID NO:2), Ala-Ala-Pro-Leu (SEQ ID NO:3), Ala-Ala-Pro-Phe (SEQ ID NO:4), Ala-Ala-Pro-Ala (SEQ ID NO:5) or Ala-Tyr-Leu-Val (SEQ ID NO:6).

In other embodiments, the protease is a matrix metalloproteinase, in particular MMP-2 or MMP-9. These matrix metalloproteinases are elevated in chronic wounds such as venous ulcers, diabetic ulcers and pressure sores. In these embodiments, the cleavable linker may comprise the oligopeptidic sequence -Gly-Pro-Y-Gly-Pro-Z- (SEQ ID NO:7), -Gly-Pro-Leu-Gly-Pro-Z- (SEQ ID NO:8), -Gly-Pro-Ile-Gly-Pro-Z- (SEQ ID NO:9), or -Ala-Pro-Gly-Leu-Z- (SEQ ID NO:10), where Y and Z are amino acids.

In other embodiments, the protease is a collagenase. Collagenase is elevated in chronic wounds such as venous ulcers, diabetic ulcers and pressure sores. In these embodiments, the cleavable linker may comprise the oligopeptidic sequence -Pro-Leu-Gly-Pro-D-Arg-Z- (SEQ ID NO:11), -Pro-Leu-Gly-Leu-Leu-Gly-Z- (SEQ ID NO:12), -Pro-Gln-Gly-Ile-Ala-Gly-Trp- (SEQ ID NO: 13), -Pro-Leu-Gly-Cys (Me)-His- (SEQ ID NO: 14), -Pro-Leu-Gly-Leu-Trp-Ala- (SEQ ID NO: 15), -Pro-Leu-Ala-Leu-Trp-Ala-Arg- (SEQ ID NO: 16), or -Pro-Leu-Ala-Tyr-Trp-Ala-Arg- (SEQ ID NO:17), where Z is an amino acid.

In other embodiments, the protease is a gelatinase. Gelatinase is elevated in chronic wounds such as venous ulcers, diabetic ulcers and pressure sores. In these embodiments, the cleavable linker may comprise the oligopeptidic sequence -Pro-Leu-Gly-Met-Trp-Ser-Arg- (SEQ ID NO:18).

In other embodiments, the protease is thrombin. In these embodiments, the cleavable linker may comprise the oligopeptidic sequence -Gly-Arg-Gly-Asp- (SEQ ID NO:19), -Gly-Gly-Arg-, -Gly-Arg-Gly-Asp-Asn-Pro- (SEQ ID NO:20), -Gly-Arg-Gly-Asp-Ser- (SEQ ID NO:21), -Gly-Arg-Gly-Asp-Ser-Pro-Lys- (SEQ ID NO:22), -Gly-Pro-Arg-, -Val-Pro-Arg-, or -Phe-Val-Arg-.

In other embodiments, the protease is stromelysin. In these embodiments, the cleavable linker may comprise the oligopeptidic sequence -Pro-Tyr-Ala-Tyr-Trp-Met-Arg- (SEQ ID NO:23).

In other embodiments the protease is a kallikrein. The term "a kallikrein" refers to all serine proteases, whose activation is associated with the degradation of kininogen to form kinins, which are implicated in the onset of pain. Suitable peptide sequences for use in cleavable substrates for kallikrein include -Phe-Arg-Ser-Ser-Arg-Gln- (SEQ ID NO:24) or -Met-Ile-Ser-Leu-Met-Lys-Arg-Pro-Gln- (SEQ ID NO:25) that can be degraded by kallikrein at Lys-Arg or Arg-Ser bonds.

In addition to the proteases, it is also envisaged that the enzyme could be, for example, an antibacterial chitinase or chitosanase such as lysozyme (elevated in infected wounds), in which case the substrate for the enzyme would be a polysaccharide or oligosaccharide comprising D-glucosamine or N-acetyl D-glucosamine residues. For example, the active agent and the inhibitor could be dispersed in a matrix of chitin or chitosan.

Preferably, the enzyme is not a kallikrein. Preferably, the enzyme is a protease other than a kallikrein, for example an elastase, a collagenase, a gelatinase or a matrix metalloproteinase.

In the wound dressing materials according to the present invention, the therapeutic agent is suitably selected from the group consisting of a reactive oxygen scavenger, an antimicrobial agent, a pain relieving agent, a growth factor or mixtures thereof.

The reactive oxygen scavenger may be selected from the group consisting of antioxidant phenol derivatives, vitamin E, methyl peroxide antioxidants, stilbenes, gallocatechins, ubiquinol, retinoids, vitamin A, vitamin C, N-acetyl cysteine, selenium and its compounds, zinc and its compounds, glutathione, carotenoids, papai, thioproline, albumin, chlorophyllin, antioxidant dyestuffs, and mixtures thereof.

The term "dyestuff" refers to a material that is useful as a colorant for textile materials, that is to say an organic compound that is strongly light-absorbing in the visible region 400-700 nm. In certain embodiments, the antioxidant dyestuff is selected from the group consisting of aniline dyes, acridine dyes, thionine dyes, bis-naphthalene dyes, thiazine dyes, azo dyes, anthraquinone dyes, and mixtures thereof. For example, the antioxidant dyestuff may be selected from the group consisting of gentian violet, aniline blue, methylene blue, crystal violet, acriflavine, 9-aminoacridine, acridine yellow, acridine orange, proflavin, quinacrine, brilliant green, trypan blue, trypan red, malachite green, azacrine, methyl violet, methyl orange, methyl yellow, ethyl violet, acid orange, acid yellow, acid blue, acid red, thioflavin, alphazurine, indigo blue, methylene green, and mixtures thereof.

The antioxidant dyestuff may be present in the wound dressing material according to the invention in an amount of from about 0.05% to about 5 wt. %, typically about 0.2 to about 2 wt. % based on the dry weight of the material.

The antimicrobial agent may be selected from the group consisting of antiseptics and antibiotics and mixtures thereof. Suitable antibiotics include peptide antimicrobials (e.g. defensins, Magainin, synthetic derivatives of them) tetracycline, penicillins, terramycins, erythromycin, bacitracin, neomycin, polymycin B, mupirocin, clindamycin and mixtures thereof. Suitable antiseptics include silver sulfadiazine, chlorhexidine, povidone iodine, triclosan, other silver salts and colloidal silver, sucralfate, quaternary ammonium salts and mixtures thereof.

The pain relieving agent may be selected from the group consisting of an anaesthetic, an analgesic, an antiinflammatory or mixtures thereof. Suitable anaesthetics include lidocaine or novocaine. Suitable analgesics include non-steroidal anti-inflammatory drugs (NSAIDs). Suitable antiinflammatory agents include steroids such as prostaglandins.

The growth factor may be selected from the group consisting of platelet derived growth factor (PDGF), fibroblast growth factor (FGF), transforming growth factor beta (TGF- β), epidermal growth factor (EGF), vascular endothelial growth factor (VEGF) and insulin-like growth factor (IGF), and mixtures thereof.

The enzyme inhibitor may be selected from the group consisting of Tissue Inhibitor of Metalloproteinase (TIMP), 4-(2-aminoethyl)benzenesulfonyl fluoride (AEBSF), antithrombin, (p-Amidinophenyl)methanesulfonyl fluoride (APMSF), Aprotinin, diisopropylfluorophosphate (DFP), phenyl methyl sulfonyl fluoride (PMSF), Antipain, Chymostatin, Leupeptin, Tosyl-lysine chloromethylketone (TLCK), Tosyl-phenyl chloromethylketone (TPCK), L-trans-epoxysuccinylleucylamido (4-guanidino) butane E-64, Amastatin, Bestatin, Diprotin, Ethylenediamine tetra-acetic acid (EDTA), pepstatin and mixtures thereof. Kallikrein inhibitors may be selected from the group consisting of aprotonin, kallistatin, nafamostat mesilate, protease inhibitor-6 (as described in U.S. Pat. No. 6,472,143), and mixtures thereof.

The wound dressing materials according to the present invention may be provided in the form of beads, flakes, powder, and preferably in the form of a film, a fibrous pad, a web, a woven or non-woven fabric, a freeze-dried sponge, a foam or combinations thereof. In certain embodiments, the polymer is selected from the group consisting of woven fabrics, knitted fabrics, and nonwoven fabrics, all of which may be made by conventional methods. In other embodiments, the material may comprise (or consist essentially of) a freeze-dried sponge or a solvent-dried sponge.

The wound dressing material may be in the form of a solid, or a semi-solid ointment or gel. Preferably, the wound dressing material comprises only up to 20% by weight, preferably less than 10% by weight of water. The relatively low water content improves the stability of the material and makes it possible to sterilize by heat or irradiation without loss of activity. The material may also contain 0-40% by weight, preferably 0-25% by weight of a plasticiser, preferably a polyhydric alcohol such as glycerol. All of the above percentages are on a dry weight basis.

Preferred wound dressing materials according to the present invention are antioxidant wound dressings wherein the therapeutic agent is a reactive oxygen scavenger, the linker comprises a substrate oligopeptide for a collagenase, an elastase, MMP-2, MMP-9 or gelatinase, and the inhibitor is a metalloproteinase inhibitor such as TIMP, Amastatin, Bestatin, Diprotin, or EDTA. Dressings of this type can provide a controlled, low level of reactive oxygen species in the wound fluid. When the desired low level is exceeded, the reactive oxygen species stimulate the production of matrix metalloproteinases in the wound fluid, which then trigger the release of the reactive oxygen scavenger and the MMP inhibitor from the dressing material. The inhibitor acts to neutralise the MMP's, and thereby prevents excessive release of oxygen scavenger from the dressing material.

Consequently, the antioxidant wound dressing material according to the present invention has a greater free radical activity, that is to say an antioxidant activity, in the presence of a metalloproteinase enzyme than in the absence of said enzyme.

Antioxidant activity may be measured by the diphenylpicrylhydrazyl (DPPH) test, for example as percentage reduction in absorbance at 524 nm after 4 hours of a 0.5% w/v dispersion of the polysaccharide in $10^{-4}$ M DPPH, as described further in U.S. Pat. No. 5,667,501. Preferably the percentage reduction in absorbance in the DPPH test is at least about 25%, more preferably at least about 50%, and most preferably at least about 75%.

Alternatively or additionally, the antioxidant activity may be measured by its ability to inhibit the oxidation of ABTS (2,2'-azino-di-[3-ethylbenzthiazoline sulfonate]) by a peroxidase.

The wound dressing material according to the present invention is preferably sterile and packaged in a microorganism-impermeable container.

Preferably, the material according to the present invention will absorb water or wound fluid and hence become wet, swell or become a gelatinous mass but will not spontaneously dissolve or disperse therein. That is to say, it is hydrophilic but has a solubility of preferably less than about 1 g/liter in water at 25° C. Low solubility renders such materials especially suitable for use as wound dressings to remove reactive oxygen species from the wound fluid.

The properties of the materials according to the present invention suggest applications in a range of medical applications, including the treatment of acute surgical and traumatic wounds, burns, fistulas, venous ulcers, arterial ulcers, pressure sores (otherwise known as decubitus ulcers), diabetic ulcers, ulcers of mixed aetiology, and other chronic or necrotic wounds and inflammatory lesions and disorders.

In a second aspect, the present invention provides a wound dressing comprising a wound dressing material according to the first aspect of the invention.

The wound dressing is preferably in sheet form and comprises an active layer of the wound dressing material according to the invention. The active layer would normally be the wound contacting layer in use, but in some embodiments it could be separated from the wound by a liquid-permeable top sheet. Preferably, the area of the active layer is from about 1 $cm^2$ to about 400 $cm^2$, more preferably from about 4 $cm^2$ to about 100 $cm^2$.

In certain embodiments, the wound dressing further comprises a backing sheet extending over the active layer opposite to the wound facing side of the active layer. The backing sheet may be larger than the active layer such that a marginal region of width 1 mm to 50 mm, preferably 5 mm to 20 mm extends around the active layer to form a so-called island dressing. In such cases, the backing sheet is preferably coated with a pressure sensitive medical grade adhesive in at least its marginal region.

Suitably, the backing sheet is substantially liquid-impermeable. The backing sheet is preferably semipermeable. That is to say, the backing sheet is preferably permeable to water vapour, but not permeable to liquid water or wound exudate. Preferably, the backing sheet is also microorganism-impermeable. Suitable continuous conformable backing sheets will preferably have a moisture vapor transmission rate (MVTR) of the backing sheet alone of 300 to 5000 $g/m^2/24$ hrs, preferably 500 to 2000 $g/m^2/24$ hrs at 37.5° C. at 100% to 10% relative humidity difference. The backing sheet thickness is preferably in the range of 10 to 1000 micrometers, more preferably 100 to 500 micrometers. It has been found that such moisture vapor transmission rates allow the wound under the dressing to heal under moist conditions without causing the skin surrounding the wound to macerate.

Suitable polymers for forming the backing sheet include polyurethanes and poly alkoxyalkyl acrylates and methacrylates such as those disclosed in GB-A-1280631. Preferably, the backing sheet comprises a continuous layer of a high density blocked polyurethane foam that is predominantly closed-cell. A suitable backing sheet material is the polyurethane film available under the Registered Trade Mark ESTANE 5714F.

The adhesive (where present) layer should be moisture vapor transmitting and/or patterned to allow passage of water vapor therethrough. The adhesive layer is preferably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is preferably 20 to 250 g/m, and more preferably 50 to 150 g/m$^2$. Polyurethane-based pressure sensitive adhesives are preferred.

Further layers of a multilayer absorbent article may be built up between the active layer and the protective sheet. For example, these layers may comprise an absorbent layer between the active layer and the protective sheet, especially if the dressing is for use on exuding wounds. The optional absorbent layer may be any of the layers conventionally used for absorbing wound fluids, serum or blood in the wound healing art, including gauzes, nonwoven fabrics, superabsorbents, hydrogels and mixtures thereof. Preferably, the absorbent layer comprises a layer of absorbent foam, such as an open celled hydrophilic polyurethane foam prepared in accordance with EP-A-0541391, the entire content of which is expressly incorporated herein by reference. In other embodiments, the absorbent layer may be a nonwoven fibrous web, for example a carded web of viscose staple fibers. The basis weight of the absorbent layer may be in the range of 50-500 g/m$^2$, such as 100-400 g/m$^2$. The uncompressed thickness of the absorbent layer may be in the range of from 0.5 mm to 10 mm, such as 1 mm to 4 mm. The free (uncompressed) liquid absorbency measured for physiological saline may be in the range of 5 to 30 g/g at 25°. Preferably, the absorbent layer or layers are substantially coextensive with the active layer.

The wound facing surface of the dressing is preferably protected before use by a removable cover sheet. The cover sheet is normally formed from flexible thermoplastic material. Suitable materials include polyesters and polyolefins. Preferably, the adhesive-facing surface of the cover sheet is a release surface. That is to say, a surface that is only weakly adherent to the active layer and the adhesive on the backing sheet to assist peeling of the adhesive layer from the cover sheet. For example, the cover sheet may be formed from a non-adherent plastic such as a fluoropolymer, or it may be provided with a release coating such as a silicone or fluoropolymer release coating.

Typically, the wound dressing according to the present invention is sterile an packaged in a microorganism-impermeable container.

In a third aspect, the present invention provides the use of a material according to the present invention for the preparation of a dressing for use in the treatment of a wound.

In a further aspect, the present invention provides a method of treatment of a mammalian wound comprising applying to the wound a therapeutically effective amount of a wound dressing material according to the present invention.

What is claimed is:

1. A wound dressing material for controlled activation of a wound healing therapeutic compound in the presence of an enzyme, comprising:
   a medically acceptable polymer;
   a therapeutic agent comprising a reactive oxygen scavenger;
   an inhibitor of the enzyme comprising a metalloproteinase inhibitor; and
   a linker group cleavable by the enzyme, wherein the therapeutic agent is conjugated to the inhibitor by the linker group.

2. A wound dressing material according to claim 1, wherein the reactive oxygen scavenger is selected from the group consisting of antioxidant phenol derivatives, vitamin E, methyl peroxide antioxidants, stilbenes, gallocatechins, ubiquinol, retinoids, vitamin A, vitamin C, N-acetyl cysteine, selenium and its compounds, zinc and its compounds, glutathione, carotenoids, papai, thioproline, albumin, chlorophyllin, antioxidant dyestuffs, and mixtures thereof.

3. A wound dressing material according to claim 1, wherein the metalloproteinase inhibitor is selected from the group consisting of Tissue Inhibitor of Metalloproteinase (TIMP), Amastatin, Bestatin, Diprotin, and Ethylenediamine tetra-acetic acid (EDTA).

4. A wound dressing material according to claim 1, wherein the linker group comprises a substrate oligopeptide for the enzyme.

5. A wound dressing material according to claim 1, wherein the enzyme is an elastase and wherein the linker group comprises a substrate oligopeptide for an elastase.

6. A wound dressing material according to claim 1, wherein the medically acceptable polymer comprises a synthetic polymer.

7. A wound dressing material according to claim 6, wherein the synthetic polymer is selected from the group consisting of polyvinyl alcohol, polyethylene glycerol, PVP, polyolefins, fluoropolymers, hydropolymers from vinyl esters, vinyl esters, carboxy vinyl monomers, meth(acrylic) acid, acrylamide, N-vinyl pyrrolidone, acylamidopropanem acylamidopropane, maleic acid, NN-dimethylacrylamide diacetone acrylamide acryloyl, morpholine, non-ionic surfactants, polyalkoylated alcohols, alkyl or dialkyl polyglycerol compounds, polyethyloxylated alcohols, and polymers of acrylamide.

8. A wound dressing material according to claim 1, wherein the medically acceptable polymer comprises a natural polymer.

9. A wound dressing material according to claim 8, wherein the natural polymer is selected from the group consisting of carbohydrates, natural peptides or proteins, modified biopolymers, and semi synthetic peptides.

10. A wound dressing material according to claim 1, wherein the therapeutic agent and the inhibitor are each conjugated to the medically acceptable polymer.

11. A wound dressing material according to claim 1, wherein elevated levels of the enzyme are associated with pain, wound infection, or wound chronicity.

12. A wound dressing material according to claim 1, wherein the enzyme is a protease, and the linker group comprises an oligopeptidic sequence which is a substrate for the protease.

13. A wound dressing material according to claim 12, wherein the protease is a matrix metalloproteinase and wherein the oligopeptidic sequence comprises or consists of -Gly-Pro-Y-Gly-Pro-Z- (SEQ ID NO: 7), -Gly-Pro-Leu-Gly-Pro-Z- (SEQ ID NO: 8), -Gly-Pro-Ile-Gly-Pro-Z- (SEQ ID NO: 9), or -Ala-Pro-Gly-Leu-Z- (SEQ ID NO: 10), where Y and Z are amino acids.

14. A wound dressing comprising a wound dressing material according to claim 1.

15. A wound dressing material for controlled activation of a wound healing therapeutic compound, comprising:
- a medically acceptable polymer;
- a wound healing therapeutic agent comprising a reactive oxygen scavenger;
- an inhibitor of an enzyme; and
- a linker group cleavable by the enzyme, wherein the wound healing therapeutic agent is conjugated to the inhibitor by the linker group in an agent/inhibitor conjugate;
- wherein the agent/inhibitor conjugate is operable to release the wound healing therapeutic agent and the inhibitor and to thereby increase the activity of both the agent/inhibitor conjugate when the agent/inhibitor conjugate contacts a wound fluid containing the enzyme.

16. A wound dressing material according to claim 15, wherein the reactive oxygen scavenger is selected from the group consisting of antioxidant phenol derivatives, vitamin E, methyl peroxide antioxidants, stilbenes, gallocatechins, ubiquinol, retinoids, vitamin A, vitamin C, N-acetyl cysteine, selenium and its compounds, zinc and its compounds, glutathione, carotenoids, papai, thioproline, albumin, chlorophyllin, antioxidant dyestuffs, and mixtures thereof.

17. A wound dressing material according to claim 15, wherein the inhibitor is selected from the group consisting of Tissue Inhibitor of Metalloproteinase (TIMP), 4-(2-aminoethyl)benzenesulfonyl fluoride AEBSF, antithrombin, (p-Amidinophenyl)methanesulfonyl fluoride APMSF, Aprotinin, diisopropylfluorophosphate DFP, phenyl methyl sulfonyl fluoride PMSF, Antipain, Chymostatin, Leupeptin, Tosyl-lysine chloromethylketone TLCK, Tosyl-phenyl chloromethylketone TPCK, L-trans-epoxysuccinylleucylamido (4-guanidino) butane E-64, Amastatin, Bestatin, Diprotin, Ethylenediamine tetra-acetic acid (EDTA), pepstatin and mixtures thereof.

* * * * *

UNITED STATES PATENT AND TRADEMARK OFFICE
CERTIFICATE OF CORRECTION

PATENT NO. : 9,687,581 B2
APPLICATION NO. : 14/507099
DATED : June 27, 2017
INVENTOR(S) : Breda Mary Cullen Page 1 of 2

It is certified that error appears in the above-identified patent and that said Letters Patent is hereby corrected as shown below:

On the Title Page

Column 2, under (Other Publications)
Line 9, delete "marcomolecules" and insert -- macromolecules --, therefor.

Column 2, under (Abstract)
Line 9, delete "would" and insert -- wound --, therefor.

In the Specification

Column 1
Lines 43-44, delete "superoxideradical" and insert -- superoxide radical --, therefor.

Column 2
Line 63, delete "a the" and insert -- the --, therefor.

Column 3
Line 61, delete "NN-dimethylacrylamide" and insert -- N,N-dimethylacrylamide --, therefor.

Column 4
Lines 10-11, delete "methyacrylamide" and insert -- methacrylamide --, therefor.

Column 6
Line 55, delete "chiorhexidine," and insert -- chlorhexidine, --, therefor.

Column 7
Line 16, delete "aprotonin," and insert -- aprotinin, --, therefor.

Column 9
Line 10, delete "g/m," and insert -- $g/m^2$, --, therefor.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,687,581 B2

Column 10
Line 20, delete "an" and insert -- and --, therefor.

In the Claims

Column 18
Line 36, in Claim 7, delete "NN-dimethylacrylamide" and insert -- N,N-dimethylacrylamide --, therefor.